United States Patent [19]

Severinghaus et al.

[11] 4,291,705
[45] Sep. 29, 1981

[54] NEUROMUSCULAR BLOCK MONITOR

[75] Inventors: John W. Severinghaus, Ross; Edwin M. Severinghaus, Corte Madera, both of Calif.

[73] Assignee: The Regents of the University of California, Berkeley, Calif.

[21] Appl. No.: 73,889

[22] Filed: Sep. 10, 1979

[51] Int. Cl.³ ............................................. A61B 5/05
[52] U.S. Cl. ................................. 128/733; 128/741
[58] Field of Search .................. 128/630, 731–733, 128/774, 213, 741

[56] References Cited

U.S. PATENT DOCUMENTS

| 2,690,178 | 9/1954 | Bickford | 128/213 |
|---|---|---|---|
| 3,364,929 | 1/1968 | Ide et al. | 128/733 |
| 3,513,834 | 5/1970 | Suzuki et al. | 128/731 |
| 3,565,080 | 2/1971 | Ide | 128/422 |
| 3,774,593 | 11/1973 | Hakata et al. | 128/733 |
| 3,898,983 | 8/1975 | Elam | 128/733 |
| 3,905,355 | 9/1975 | Brudny | 128/733 |
| 3,916,876 | 11/1975 | Freeman | 128/733 |
| 4,148,303 | 4/1979 | Cohen | 128/733 |

FOREIGN PATENT DOCUMENTS

| 229750 | 3/1969 | U.S.S.R. | 128/733 |
|---|---|---|---|
| 553968 | 4/1977 | U.S.S.R. | 128/733 |

OTHER PUBLICATIONS

Gigauri, et al., "A New Instrument for Monitoring of Muscle Relaxation of a Patient, " Trans. from Meditsinskaya Tekhinika, No. 4, Jul.–Aug., 1974, pp. 232–234.
Thomas, H. "Muscle Measurement and Therapy Instruments", Ch. 10 in *Handbook of Biomedical Instrumentation & Measurement*, Reston Publ. Co., ©1974 pp. 321–349.
Lee, et al., "A New Instr. for Cont. Recording of Evoked Compound EMG in the Clin. Setting", Anest & Analges ... Curr. Researches V56No2 Mar. –Apr. 1977 pp. 260–270.
Aminoff, M. J. "The Apparatus; non EMG System,", Ch. 4 in *EMG in Clin Practice* Wesley Publ. 1978.

Primary Examiner—Robert W. Michell
Assistant Examiner—Francis J. Jaworski
Attorney, Agent, or Firm—Limbach, Limbach & Sutton

[57] ABSTRACT

To determine the degree of neuromuscular blockage, the apparatus of the invention electrically, supramaximally stimulates the motor nerve of a patient by stimulus means, applies the resulting electromyogram (EMG) produced by the muscle associated with that motor nerve and integrates the amplified EMG with respect to time. The integrated, amplified EMG is then displayed. In a preferred embodiment of the invention means are also provided for displaying the integrated, amplified EMG, taken after a muscle relaxant has been administered to the patient, as a ratio of a control EMG taken with the apparatus before the administration of the drug.

9 Claims, 3 Drawing Figures

NEUROMUSCULAR BLOCK MONITOR

BACKGROUND OF THE INVENTION

The present invention relates to devices and methods for determining the degree of neuromuscular blockage produced by the use of muscle relaxant drugs to a patient. More specifically the present invention relates to apparatus for monitoring neuromuscular transmission.

During many surgical operations it is important to relax the patient's muscles by administering drugs such as curare, and the like. If a dose of the relaxant drug is given in the correct amount, the effects of the drug will wear off after surgery and the patient will regain his or her ability to breathe naturally, with little after-effects. If, however, an overdose is given an extended paralysis and other after effects may occur which are highly undesirable. What is needed is a way to continually measure the percentage of the completeness of the neuromuscular block produced by the muscle relaxant drug both during and after the operation. Clinical experience has shown that optimal muscle relaxation is obtained when a block is about 95% complete (5% of control). A more complete block is usually not needed and may lead to prolonged recovery or difficulty in reversing the blockage.

After surgery antagonist drugs are administered to the patient to reverse the effect of the muscle relaxants. In some cases, however, the blocking drugs originally administered to the patient may outlast the antagonists, resulting in a recurrence of weakness in the recovery room. It is therefore important to be able to monitor the degree of neuromuscular blockage during the administration of the antagonist drugs. The way in which the antagonist drugs work is to help the patient's body utilize chemicals produced within the nerve cells to reestablish control. These chemicals are subject to depletion as control is regained, producing an effect known as fading. In such a condition the initial amount of control in response to a single stimulus may be satisfactory but this control fades with repeated stimuli following immediately after the first stimulus. To check for fading it is necessary to measure the amount of neuromuscular blockage using tetanus stimulation.

Among the prior art methods and devices for monitoring neuromuscular blockage the most widely used is a portable battery operated stimulator without a meter. The anesthesiologist watches the movement of a muscle such as a finger, thumb or facial muscle after a twitch or tetanic stimulus. For research purposes, and occasionally for clinical monitoring, some prior art devices have employed strain gauges or force transducers which are taped to a digit to permit recording of the strength of the contraction. See for example U.S. Pat. Nos. 3,898,983 and 3,565,080 (Ide).

This technique requires a separate amplifier and recorder. Furthermore such devices are highly inaccurate and subject to spurious signals as the digit to which the strain gauge has been taped is moved during surgery, thus providing unreliable information. Another problem with measuring the twitch of a digit or other muscle as an indication of neuromuscular blockage is that the two are not linearly related. In some cases the muscular twitch will disappear before the EMG is fully blocked.

Another proposal is to record the EMG response from the patient. The EMG signal impulse is too fast for conventional direct writing pen recorders and the like, so that users have employed oscilloscopes and photographic recording. A recent device has been reported in which an EMG amplifier digitizes the response at 0.25 millisecond intervals and stores the digitized response in a memory, such as a magnetic tape or magnetic disc. This digitized memorized signal is then played back a few seconds later at a much slower rate into a pen recorder or the like. Aside from the time delay in obtaining the response this device also requires elaborate and expensive electronic equipment.

SUMMARY OF THE INVENTION

The above and other disadvantages of prior art neuromuscular transmission monitoring apparatus are overcome by the present invention which comprise means for electrically, supramaximally stimulating a motor nerve, means connected to the stimulus means for receiving and amplifying the resulting electromyogram (EMG) produced by the muscle associated with the motor nerve, means connected to the EMG amplifier means for integrating the amplified EMG with respect to time, and means connected to the integrator means for displaying the integrated, amplified EMG.

In the preferred embodiment of the invention the display means further comprise simple and direct means for displaying the ratios of EMG's obtained from a patient after the administration of the muscle relaxant drug to a reference standard (ie. control) EMG which is taken with the same monitoring apparatus but before the administration of the muscle relaxant drug. In this embodiment the readout from the apparatus is expressed as a percentage of the control response.

The stimulus means include mode control means for selectively causing the production of either a single pulse (twitch), a train of pulses (tetanus), or a train of a predetermined number of pulses at regular intervals. Further included are iterating means to automatically cause the stimulus means to repeatedly generate stimulus pulses at predetermined intervals. The stimulus pulses which are repeated can be either the twitch, tetanus or train of predetermined number of pulses.

The amplifier means include a gate which is triggered by the stimulus pulse for gating the amplifier means on a predetermined time after the stimulus pulse and for thereafter holding the amplifier means on for predetermined period of time to allow the integration of the resulting EMG. In the preferred embodiment the amplifier means include rectifier means for passing only negative polarity EMG's of the appropriate frequency. This feature, combined with the gating feature, avoids artifacts from the stimulator and other noise sources.

In one embodiment of the invention the display means include a digital circuit for automatically comparing the resulting EMG to the control EMG and digitally displaying the output as a percentage of the control EMG.

In contrast to some prior art devices which simply measured the EMG by mechanical transducer means, for example, the response signal measured by the present invention is instantaneously processed by integration of the EMG negative output, thereby giving area rather than peak height. Some drugs and conditions cause a broadening of the response due to delayed conduction in some neural or motor units, and under such circumstances, the area under the response is a better index of total transmission than is peak height. The present invention avoids the need to mechanically fix a force transducer to a digit, and to immobilize the hand and guard it from disturbance by surgeons and nurses standing at the operating table. It also avoids the use of such fragile and expensive transducers.

Furthermore the present invention permits improved monitoring in clinical anesthetic practice, by giving a quantitative, continuous indication of the degree of neuromuscular blockage, thus permitting more careful determination of the dosage of neuromuscular blocking drugs and their antagonists. With present visual monitoring of the muscular response, it may be difficult to determine whether a weak response is present or not.

Since the device of the present invention is portable and self-contained, it may be left attached to the patient after surgery, during transport to the recovery area, and during recovery, to monitor the return of neuromuscular transmission. As mentioned above, this is an important feature since in some cases, the blocking drugs may outlast the antagonists, resulting in a recurrence of weakness in the recovery room.

Since the stimulator and EMG amplifier are combined, the synchronization of the amplifier gate is built in. In all units now in use, a synchronization pulse must be externally connected from the stimulator to the amplifier for accuracy. The voltage and current characteristics of such sync signals are not standardized among various units.

It is therefore an object of the present invention to provide a portable neuromuscular blockage monitor.

It is another object of the invention to provide a neuromuscular blockage monitor in which the stimulator and response meter are combined into a single unit.

It is yet another object of the invention to provide a neuromuscular blockage monitor which requires no connection to electrical power lines.

It is a further object of the invention to provide a neuromuscular blockage monitor in which the neuromuscular response during blockage is measured and displayed directly as a percentage of the control response.

It is yet a further object of the present invention to provide a neuromuscular blockage monitor which is responsive to the area of EMG response rather than to peak height.

It is yet another object of the invention to provide a neuromuscular blockage monitor having easily selected modes of operation including twitch, train of four, or tetanus stimulation pulses.

It is still another object of the invention to provide a neuromuscular blockage monitor which repeatedly and automatically stimulates and monitors at predetermined time intervals.

The foregoing and other objectives, features and advantages of the invention will be more readily understood upon consideration of the following detailed description of certain preferred embodiments of the invention, taken in conjunction with the accompanying drawings.

DETAILED DESCRIPTION OF CERTAIN PREFERRED EMBODIMENTS

Figure 1:
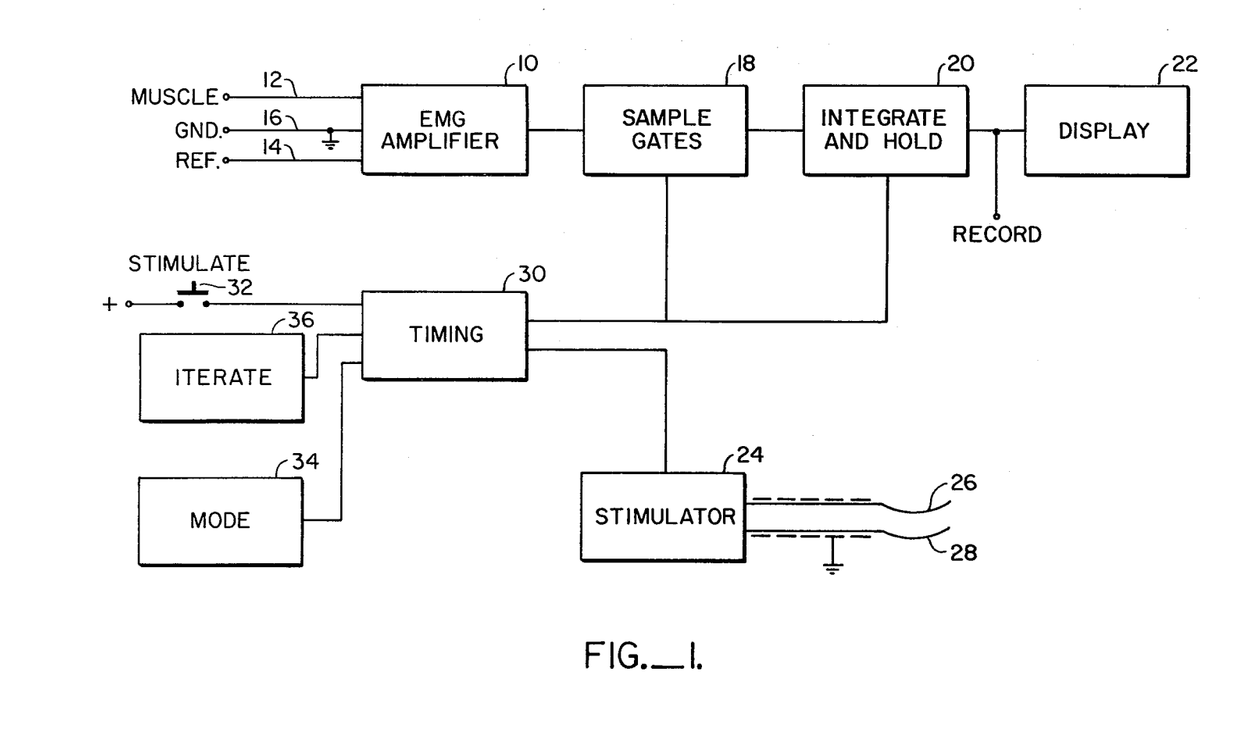
FIG. 1 is a block, schematic diagram of the neuromuscular block monitor according to the invention.

Referring now more particularly to FIG. 1 a differential amplifier 10 receives the electromyogram signal from two electrodes 12 and 14, which are self-adhesive skin surface, EKG-type electrodes. Electrode 12 is placed over a particular muscle and the reference electrode 14 is placed nearby on the patient's skin, but not on that muscle. The ground electrode, of course, is attached to the patient at some other location. Amplified EMG signals from the amplifier 10 are supplied to a sample gate 18. The purpose of the sample gate is to allow the amplification of only negative EMG signals received 1.5 milliseconds after the stimulus is applied and for a duration of 8 milliseconds. The frequency response of the amplifier 10 is constant ±3 db from 10 Hz to above 2 KHz. The amplified signals passed by gate 18 are supplied to an integrator 20 which integrates and stores or holds the area under EMG response curve. The integrated signal from the integrator 20 is supplied to a display 22.

A stimulator 24 is connected to the patient by a pair of skin surface electrodes 26 and 28. The active stimulus electrode 26 is affixed over the motor nerve of the patient which controls the muscle over which the electrode 12 is positioned. The stimulus return electrode 28 is attached to the patient nearby the electrode 26.

The stimulator is controlled by a timing circuit 30. The timing circuit is activated initially either by a pushbutton stimulate switch 32 or automatically at timed intervals after an iterate switch 36 is operated. A mode selector switch 34 is also connected to the timing circuit to determine what type of stimulus pulse is to be supplied by the stimulator 24. As will be explained in greater detail hereinafter, the mode switch 34 allows at least four types of stimulus pulses to be applied to the patient. In the first position a single twitch pulse is supplied to the patient. In the second position a train of four such twitch pulses are supplied at half second intervals. The third and fourth positions of the mode switch apply tetanus pulses for differing periods of time to the patient. The tetanus train consists of repeating stimuli every 20 millisecond (50 Hz). In the third position of the mode switch the tetanus train lasts two seconds and in the fourth position the tetanus train lasts for 0.1 seconds.

As mentioned above the iterate switch 36 selectively causes the timing circuit 30 to repeat whatever mode was selected at predetermined timed intervals.

In operation, when the mode selector switch 34 is positioned in the twitch mode, a 0.15 millisecond square wave pulse is supplied from the stimulator to the patient through the electrodes 26 and 28 when the stimulate switch 32 is depressed. The timing circuit 30 and the sample and hold gate 18 do not begin to pass the output from the EMG amplifier 10 through to the integrator 20 until 1.5 milliseconds after the stimulus. This ensures that whatever signal is received by the electrodes 12 and 14 and is amplified by the amplifier 10 will be the true EMG in response to the stimulus and not noise or artifacts from the stimulator. The EMG amplifier 10 amplifies the EMG signal, and the negative portion of that signal is passed by the gate 18 to the integrator 20 for the following 8 milliseconds. At the end of the 8 millisecond period the timing circuit turns off the sample gate 18 and the integrated EMG output from the integrator 20 is held and displayed on the display 22.

Figure 2:
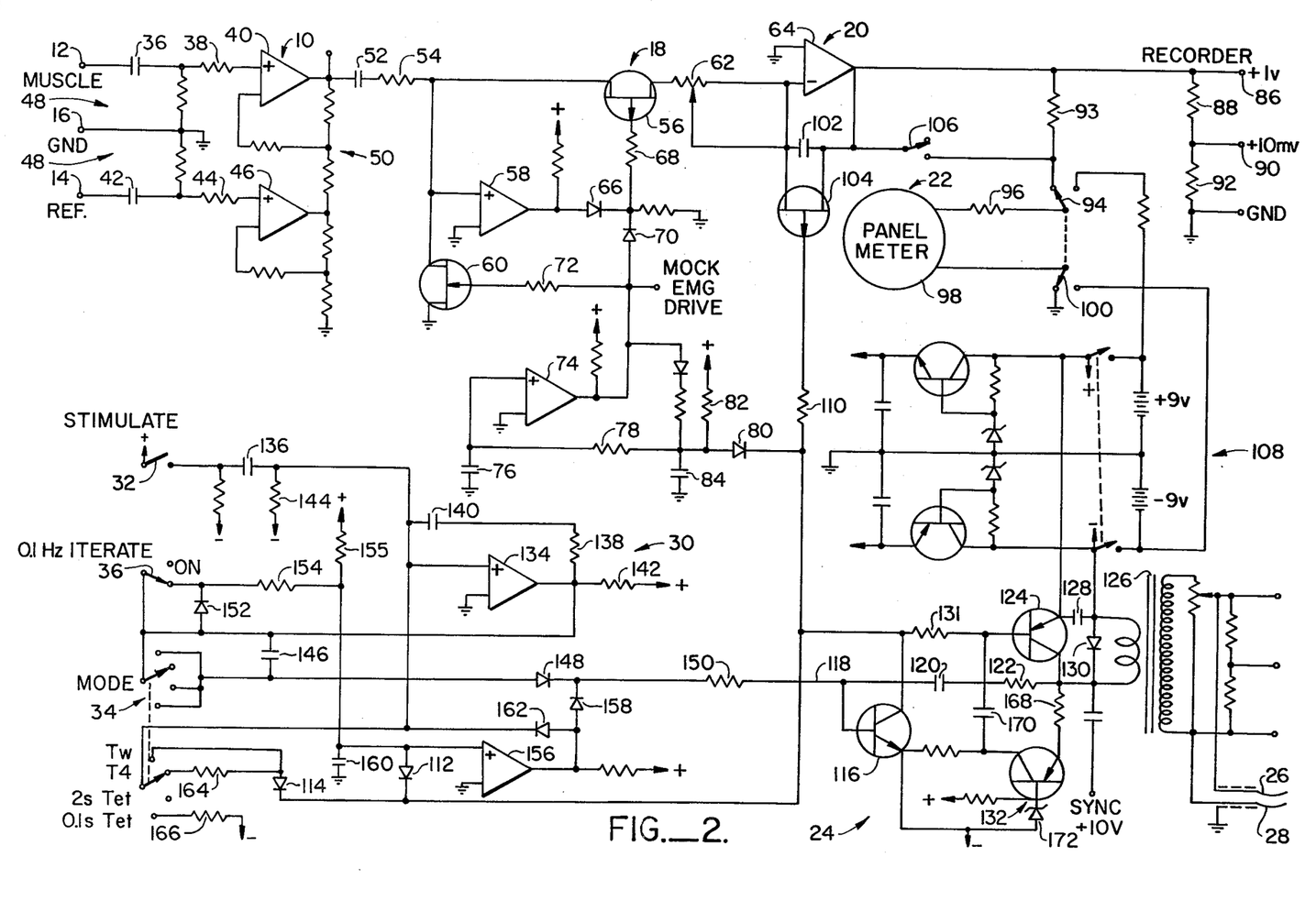
FIG. 2 is a detailed schematic diagram of the neuromuscular block monitor depicted in FIG. 1.

Referring now more particularly to FIG. 2, the system will be described in greater detail. The electrode 12 is coupled through a capacitor 36 and a resistor 38 to the plus input of a differential amplifier 40. Similarly the reference electrode 14 is coupled through a capacitor 42 and a resistor 44 to the plus input of a second differential amplifier 46. The ground electrode 16 is connected to the circuit ground and also to the mid-point of a pair of resistors 48 which are connected in series between the resistors 38 and 44. A voltage divider network 50, connected between the output of the amplifier 40, the output of the amplifier 46 and the circuit ground, subtracts the output of the amplifier 46 from the output of the amplifier 40 so that only the difference of the two outputs is fed through a capacitor 52 connected to the output of the amplifier 40. The amplifiers 40 and 46 are thus in an instrumentation configuration.

The difference signal supplied through the capacitor 52 passes through a resistor 54 to the source or drain electrode of a field effect transistor 56, to the plus input of a comparator 58, and to the source or drain electrode of a second field effect transistor 60. The other of the source or drain electrodes of the FET 60 is connected to the circuit ground as is the negative input to the comparator 58. The other of the source and drain electrodes of the FET 56 is connected through a potentiometer 62 to the negative input of an integrating, differential amplifier 64 whose other input is connected to the circuit ground.

The output of the comparator 58 is connected to the anode of the diode 66 whose cathode is connected through a resistor 68 to the negative bias controlled gate electrode of the FET 56.

The gate electrode of the FET 56 is also connected to the cathode of a diode 70 whose anode is connected through a resistor 72 to the positively controlled gate electrode of the FET 60 and the output of a comparator 74. The positive input to the comparator 74 is connected to one side of a capacitor 76, whose other side is grounded, and through a resistor 78 to the anode of a diode 80. A positive bias is provided to the input of the comparator 74 by means of a resistor 82 connected between the plus bias source of the circuit and the anode of the diode 80. A capacitor 84 is also connected between the anode of the diode 80 and the circuit ground.

In operation, unless a negative pulse is applied to the cathode of the diode 80, the output of the comparator 74 will be positive and, passing through the diode 70, will cause the FET 56 to be non-conductive and the FET 60 to be conductive, so that no signal will pass through the potentiometer 62 to the integrating amplifier 64. When a negative level is applied to the cathode of the diode 80 it will serve to discharge the capacitor 84 and then the capacitor 76 over a time period determined by the product of the resistance of the resistor 78 and the capacitance of the capacitor 76. When the capacitor 76 is no longer positive the comparator 74 will produce a negative bias and thus the FET 60 will become open circuited and the FET 56 will become conductive depending on the output of the comparator 58.

If the signal being supplied to the FET 56 through the resistor 54 is positive, the comparator 50 provides a positive bias to the FET 56, thereby causing it to become non-conductive. Negative going signals, on the other hand, drive the comparator 58 negative permitting the transistor 56 to be conductive (when comparator 74 output is also negative) and pass through the FET 56 and the resistor 62 to be integrated by the integrating amplifier 64 in a manner to be described in greater detail hereinafter. Thus only negative going signals are integrated in the applicants' device and only those signals appearing during the time period required to recharge the capacitor 76 through the resistors 78 and 82 (approximately 8 milliseconds).

The output of the integrating amplifier 64 is supplied to a recorder terminal 86. Terminal 86 is connected through a resistor 88 to an intermediate terminal 90 which, in turn, is connected through a second resistor 92 to the circuit ground. The purpose of the terminal 90 is to provide a low voltage or scaled version of the signal appearing at the terminal 86.

The output of the amplifier 64 is also connected through a resistor 93, a switch 94 and a resistor 96, in series, to one lead of a meter 98 which constitutes the display 22. The other lead of the meter 98 is connected through a second switch 100 to the circuit ground.

The integrating return path from the output of the amplifier 64 is through a capacitor 102 connected to the negative input of the amplifier 64 and to the moving contact of the potentiometer 62. An FET 104 is connected to selectively shunt the capacitor 102 when the FET 104 becomes conductive. A switch 106 is connected in parallel with the resistor 93 to provide for alternate voltage scale readings on the meter 98.

In operation, the amplified EMG signal from the differential amplifier 10 is integrated by the amplifier 64 at a rate determined by the product of the capacitor 102 and the resistance of the resistor 62. Thus the setting of the contact arm of the potentiometer 62 determines the rate of integration.

In the preferred embodiment of the invention the method under which this operation is carried out begins by providing a stimulus to the patient before the administration of the muscle relaxant. At this time the contact arm has been moved fully to the right so that the slowest rate of integration is utilized. The meter is then read for that control EMG. The meter scale will run from 0 to 100. Assuming that the meter reads some number less than 100, for example 30, then the contact arm of the potentiometer 62 is accordingly adjusted to present 30% of the full resistance of the potentiometer 62. With suitable scaling, the contact arm can simply by dialed to a number 30 on a linear indicating dial (not shown). It should be noted that the winding of the potentiometer 62 is linear so that a 30% of full scale position will present a corresponding 30% of full resistance. The next reading of a controlled stimulus signal will be full scale on the meter. Subsequent readings for EMG's produced after the administration of a muscle relaxant will produce meter readings which are some amount less than full scale and therefore can be directly read as a percentage of the controlled stimulation response. For example an EMG reading taken after the administration of a muscle relaxant which showed a meter reading of 40 would indicate that the muscle relaxant block is 60% complete (40% of control).

The switches 94 and 100 are single pole double throw switches and can be moved to an alternate position from that shown in FIG. 2 to connect the meter 98 to the batteries to check their voltage level.

The gate of the FET 104 is connected through a resistor 110 to the collector of an NPN transistor 116 which is part of the stimulator circuit 24. The emitter of the transistor 116 is connected to the negative bias terminal of the power supply 108. The base of the transistor 116 is connected to an input trigger line 118 of the stimulator circuit 24. It will be appreciated that when the transistor 116 is made conductive by the application of a current pulse to the base of 116 the collector electrode will become negative, thereby applying a negative pulse to the gate electrode of the FET 104 and causing it to become conductive. As will be explained in greater detail hereinafter, this occurs whenever the stimulator circuit 24 is triggered with the effect that the integrator circuit 20 is simultaneously reset to zero when the FET 104 becomes conductive.

The details of the stimulator circuit 24 will now be described. The trigger line 118 is connected through a capacitor 120 in series with a resistor 122 to the collector of a PNP transistor 124. The collector of the transistor 124 is connected through the primary winding of a transformer 126 to a negative terminal of the power supply 108. The emitter of the transistor 124 is connected to a positive terminal of power supply 108. A capacitor 128 is connected between the positive and negative terminals of the power supply 108. A diode 130 is connected at its anode to the negative terminal of the power supply 108 and at its cathode to the collector of the transistor 124. The base of the transistor 124 is connected through a resistor 131 to the collector of the transistor 116.

In operation, when a current is applied to the base of transistor 116 the transistor 116 becomes conductive and turns on the transistor 124, thereby providing a current pulse to the primary of the transformer 126 and a corresponding stimulus pulse to the electrode probes 26 and 28. A voltage limiting circuit 132 is connected between the collector and base of the transistor 124, through resistor 168 and capacitor 170, and the negative terminal of the power supply 108. The purpose of the circuit 132 is to regulate the pulse height of the stimulus pulse applied to the electrodes 26 and 28 independent of the load on the battery operated power supply 108. When the pulse voltage on the collector of 126 reaches the specified level set by zener diode 172, transistor 132 conducts, and sends current through capacitor 170 to prevent further increase in base current in transistor 124. Capacitor 120 and resistor 122 provide increased (decreased) base current drive to transistor 116 on the rising (falling) edge of the signal at transistor 124, thus providing faster, more stable turn on/(off) transistor 116, thereby providing a stable pulse to the patient.

The trigger pulse to the line 118 is supplied by the timing circuit 30. The timing circuit 30 comprises a comparator 134 whose positive input is connected through a capacitor 136 in series with the stimulator switch 32 to a positive terminal of the power supply 108. The output of the comparator 134 is connected through a resistor 138 in series with a capacitor 140 to the positive input of the comparator 134. The output of the comparator 134 is also connected to the positive terminal of the power supply 108 by means of a suitable biasing resistor 142. The positive input terminal of the comparator 134 is also connected to a negative terminal of the power supply 108 through a resistor 144.

When the stimulate switch 32 is closed, a positive pulse is applied to the input of the comparator 134 which amplifies the pulse and provides a positive output back to its own input through the resistor 138 and the capacitor 140. This positive output continues for about two seconds until the capacitor 140 is discharged by the resistor 144. The output of the comparator 134 will then flip suddenly to the negative power supply (due to the bias through resistor 144). Thus the time constant produced by the product of the capacitor 140 and the resistor 144 determines the duration of the positive output pulse from the comparator 134 when the stimulus switch 32 is closed.

The output of the comparator 134 is also connected through a capacitor 146 to the anode of a diode 148. The cathode of the diode 148 is connected through a resistor 150 to the trigger line 118. The output of the comparator 134 is also connected to the moving contact of the iterate switch 36 and one of the moving contacts of the mode switch 34. The fixed contact terminals of this portion of the mode switch 34 are all connected to the anode of the diode 148 with the exception of one unconnected contact at the train of four setting of the switch 34.

The iterate switch 36, when in the off position, shunts a diode 152 whose anode is connected to the output of the comparator 134 and whose cathode is connected through a resistor 154 to the positive input of a second comparator 156. When the iterate switch 36 is in the on setting it is unconnected, for purposes of the operation of the circuit.

The output of the comparator 156 is connected to the anode of a diode 158 whose cathode is connected to the cathode of diode 148. The negative input to the comparator 156 is connected to the circuit ground. The positive input to the comparator 156 is connected to the anode of the diode 112 and also through a capacitor 160 to the circuit ground. The output of the comparator 156 is further connected to the anode of a diode 162 whose cathode is connected to the moving contact of the second portion of the switch 34. The fixed contact terminals of the second portion of the switch 34 have the following connections. At the twitch setting the contact is connected to the anode of the diode 114. At the train of four setting the contact is connected through a resistor 164 to the anode of the diode 114. At the two second tetanus pulse setting the contact is unconnected and at the 0.1 second tetanus setting the contact is connected through a resistor 166 to a negative terminal of the power supply 108.

The operation of the timing circuit 30 and the stimulator 24 depend on the settings of the three switches 32, 36 and 34. The resulting EMG's in all cases will be detected, amplified, rectified, integrated and displayed in the manner heretofore described. Assuming that the iterate switch 36 is turned off and that the mode switch 34 is set in the twitch setting, when the stimulus switch 32 is pressed the comparator 134 will provide an enabling positive pulse through the switch 34, the diode 148 and the resistor 150 to the trigger line 118. When the stimulator 24 provides the stimulus pulse to the probes 26 and 28, as outlined above, a negative pulse will be sent back from the collector of the transistor 116, through the diode 114 and the second portion of the switch 34 to the positive input of the comparator 134. The effect of this negative pulse is to discharge the capacitor 140 and reset the comparator 134 to a negative output. Thus a single twitch stimulus pulse has been provided.

With the mode switch 34 set at the train of four position, as it appears in FIG. 2, closing of the stimulus switch 32 causes the comparator 134 to again provide an enabling pulse to the trigger line 118 through the capacitor 146, the diode 148 and the resistor 150. This enabling pulse is also provided to the capacitor 160 to charge it from its initial negative potential derived from the previous negative output of the comparator 134. The capacitor 160 charges to a positive potential through the switch 36 and the resistor 154 after about one-half second to produce a positive output from the comparator 156 which is supplied to the trigger line 118. This causes the stimulator to again trigger and again produce a negative reset pulse through the diode 112 to discharge the capacitor 160.

This process will be repeated as long as the output of the comparator 134 remains positive, which is for approximately two seconds. Provided the correct resistance and capacitance values have been chosen four such stimulus pulses are generated. In order to ensure that only four such pulses are provided the negative pulse occurring on the last of the four pulses, and which passes through the diode 114 and the resistor 164, serves to discharge the capacitor 140 of any remaining residual charge near the end of the two second interval. This also ensures that no significant recharging of the capacitor 160 takes place after the fourth such stimulus pulse. If this were not done then the next cycling using the comparator 156 for iteration or train of four mode would not be accurate.

With the mode switch set at either the two second tetanus or 0.1 second tetanus the output of the comparator 134 is again provided to the trigger line through the first portion of the mode switch 34, the diode 148 and the resistor 150. As long as a positive bias is provided to the trigger line 118 the stimulator will oscillate at 50 Hz with an on time of 0.15 milliseconds. The oscillation rate is a product of the resistance of the resistor 150 and the capacitance of the capacitor 120 whereas the on time of 0.15 milliseconds is determined by the product of the capacitance of the capacitor 120 and the resistance of the resistor 122. The duration of this tetanus train is determined by the product of the capacitance of the capacitor 140 and the resistance of the resistor 144 (in the two second mode) or the resistance of the resistor 166 (in the 0.1 second mode).

The purpose of the iteration switch 36 is to cause any selected mode to be repeated at approximately 10 second intervals. When the switch 36 is set to "on", ie. it is opened, then the quiescent, negative polarity output of the comparator 134 is not applied to the capacitor 160 because of the diode 152. The capacitor 160 will slowly charge to a positive polarity through a resistor 155 connected to the positive terminal of the power supply 108. Once the charge becomes positive the comparator 156 will trigger the stimulator 24 as well as supply a positive input to the comparator 134. At that point the timing circuit will behave just as though the stimulate switch 32 had been depressed and whatever mode is selected by the switch 34 will be executed. Ultimately the capacitor 160 is charged negatively by the negative pulse supplied from the stimulator circuit 24 through the diode 160. The capacitor 160 will then begin to recharge through the resistor 155. This process will be repeated at timed intervals, e.g. every 10 seconds, as determined by the product of the resistance of the resistor 155 and the capacitance of the capacitor 160.

Figure 3:
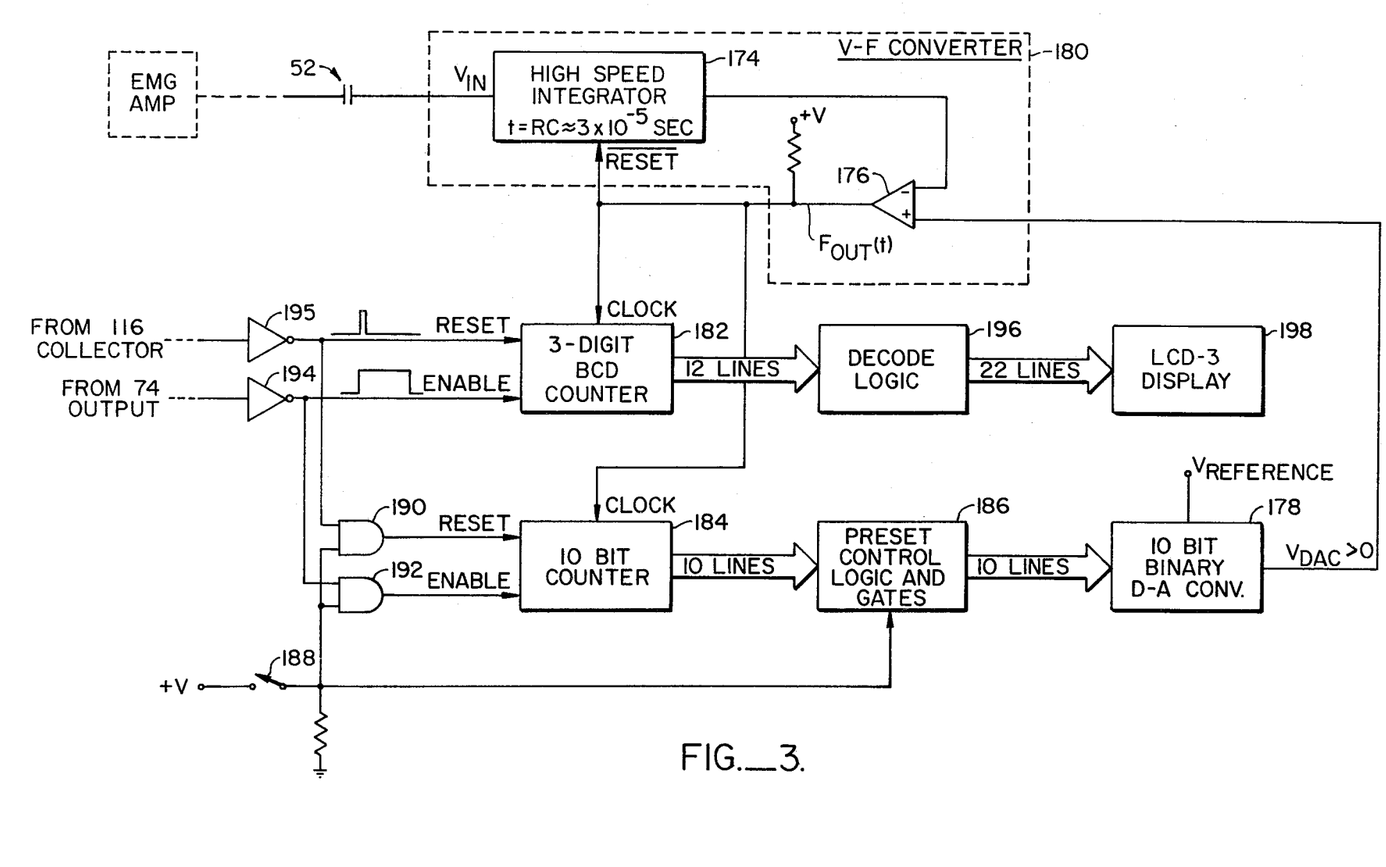
FIG. 3 is a schematic diagram of a portion of a modified embodiment of the invention.

Referring now more particularly to FIG. 3 an alternative embodiment of the present invention is illustrated in which the output display is in digital form. This embodiment may be implemented while omitting certain components from the embodiment depicted in FIG. 2 and replacing those components with circuitry shown in FIG. 3. The labeled components from FIG. 2 which are omitted are components 18, 58, 60, 62, 66, 68, 70, 72 and 110 as well as the entire meter circuit. In addition to the power and ground connections between the two sections of the circuit there are two other connections, the collector of transistor 116 is connected as shown on FIG. 3 and the output of comparator 74 is connected as shown in FIG. 3 in addition to any other connections which may be present on FIG. 2. The output of the instrumentation amplifier 10 is taken through capacitor 52 to the signal input of a high speed integrating means 174. This means may typically comprise an input resistor, a feedback capacitor and a operational amplifier. In addition there is a clamping diode and a field effect transistor. The output of the integrator 174 is fed into the inverting input of a comparator 176. The non-inverting input of the comparator 176 is driven by the output voltage of a type D to A converter 178. The function of the D to A convertor will be explained later. The output of the comparator 176 with appropriate level shifting feeds to the reset transistor within the integrator 174 and in operation the sequence is as follows.

When a negative input voltage appears at the input of the integrator 174 the output integrator is caused to ramp positive. When the voltage exceeds the output voltage of the D to A convertor 178 the output of the comparator 176 changes state going low, that is negative, and causing the reset switch on the integrator 174 to reset it to zero. As soon as the integrator 174 reaches zero, or approximately thereabouts, the comparator 176 then changes state and releases the drive to the reset transistor within the integrator 174 allowing the integrator to again begin integrating the signal. This cycle is repeated and generates a pulse train whose frequency is proportional to the input voltage divided by the D to A convertor output voltage. The transfer equation is given as follows:

$$F^{(t)}_{out} = \frac{V_{in}(t)}{V_{DAC}} \times \frac{1}{RC} H_z$$

(for negative $V_{in}$ only; $F_{out} = 0 H_z$ for $V_{in} \geq 0$)

$$V_{DAC} = -\frac{\text{"Digital In"} \times V_{ref}}{1023} \text{ Volts}$$

("Digital In" ≡ Count)

$$\text{Count} = \int_0^{8 \, m'sec} F^{(t)}_{out} \, dt \quad \text{(dimensionless)}$$

The integrator, comparator and D to A convertor output voltage form what is known in the trade as a voltage to frequency convertor 180 and may be implemented in one of several different ways. This pulse train from the comparator 176 is also fed to a counter section, which in the figure as shown consists of two different counters 182 and 184. It is possible by appropriate manipulation of digital circuitry to allow using only one counter. This pulse train from the comparator 176 goes into the clock inputs respectively of a 10 bit counter 184 and a 3 digit BCD counter 182. BCD stands for binary coded decimal. The output of the 10 bit counter 184 feeds by way of gating logic 186 to the digital inputs of the D to A convertor 178. The 10 bit counter 184 is used to collect and store the control pulse, ie. the control EMG signal as defined earlier.

The D to A convertor 178 then converts this digital representation of the control signal into a voltage representation mentioned before as the output voltage of the D to A convertor. The digital gating logic 186 is provided to allow presetting the D to A convertor 178 to a decimal value of 100 that is a binary value of 0001100100. This value of 100 is chosen so that when the control signal is stored it will be referenced to a 100 signal and therefore when the control value is fed into the 10 bit counter 184 and then back into the D to A convertor 178 at the end of the collection of the control signal, all subsequent storage signals will be referenced to the control signal divided by 100 thus giving a readout in percent. The switch 188 shown connected to the gate 186 is a normally open, momentary switch and may be defined as the control preset switch. It is held down for and during a collection of a control signal from the patient.

When the switch is closed it biases an AND and OR gates at the D to A convertor 178 to provide a decimal of 100. In addition it provides an enabling signal for the 10 bit counter 184 which is used in two ways. First this enabling signal is anded with the buffered and level shifted signal (by buffer and level shifter 195) from transistor 116 collector mentioned before, which feeds through an AND gate 190 to the reset port of the 10 bit counter 184. Thus when one is storing a control signal this 0.15 millisecond pulse from 116 collector will reset the control register to zero before the counter is to be enabled to then store the control signal. The switch connection also controls another AND gate 192. The other input of the AND gate 192 feeds from the comparator 74 output through a convertor buffer level shifter 194 to the enabling input of the 10 bit counter 184.

Returning to the 3 digit BCD counter 182, this is the display accumulator and storage counter. It also is fed by the enabling reset lines from the comparator 74 output and transistor 116 collector, respectively, which perform the same function as they did on the 10 bit counter only these are not gated by the switch 188. Thus with each stimulus and respective EMG response this counter 182 is reset and then a little bit later is allowed to accumulate counts from the voltage to frequency convertor 180. The outputs from this counter are fed into standard decoding logic 196 and converted to a format capable of driving a liquid crystal display 198. The resistor shown on the pole of the switch 188 is simply used to assure that the digital logic lines are not floating when that switch is open and may be any convenient value from 1 K to 1 megohm depending on the size circumstances. Note: All of the digital logic is presumed to be implemented in Cmos technology and is readily available in a commercial market in the United States in many different prepackaged forms. As mentioned before, it is not necessary to use two counters. An example of how to use only one counter would be to use the three digit BCD counter feeding the outputs of the decoding logic display and also feeding the outputs to three four bit batches which then feed the D to A convertor through the gating logic. A similar, but not exactly the same, method for resetting and enabling the latch is used. The advantage of using the latches is it simplifies by reducing the number of gates required to preset the D to A convertor to 100. However it has its own requirement for its own additional control circuitry in the form of 1 or 2 gates. If the latch version is used, the D to A convertor must be a three digit BCD input D to A convertor—if the 10 bit counter version is used then the D to A convertor is more simply a ten bit binary D to A convertor. The D to A convertor may be of any standard type which has a voltage output or maybe a current output type with an appended operational amplifier to convert the current into a voltage. It may use an extra low voltage reference or have its own internal voltage reference which will be scaled for the appropriate value for this particular circuit.

In either of these alternative embodiments the function of resistor 62 is changed. This resistor no longer needs to be a variable resistor. It may be a fixed resistor of appropriate value to set the time constant for the RC circuit of the integrator to appropriate value.

The sequence of events in collecting the control and then subsequently collecting and displaying a sample will now be briefly summarized. The operator of the unit selects the level of stimulus desired and sets the selector switch 34 to single twitch. The operator then presses the stimulus button 32 causing the stimulator section 24 of the circuit to apply its signal voltage to the nerve causing the muscle to put out its EMG waveform which is amplified by the amplifier as described earlier. The amplified EMG is fed through capacitor 52 and is then present during the 8 or so milliseconds duration of that response at the input to the high speed integrator 180. When the input to the high speed integrator is positive the integrator will attempt to drive this output downwards, however the clamping diode prevents it from going very far negative. When the input signal is negative the integrator quickly recovers and begins integrating in a positive direction and then goes through the sequence of events described earlier, driving the comparator 176 output state low and being reset and then again integrating upwards and subsequently doing the same thing with the comparator 176 creating the pulse train mentioned before. The switch 188 being closed has preset a value of 100 into the D to A convertor 178 which is translated into the appropriate output voltage by the D to A convertor. Thus the control EMG signal is referenced to the voltage equivalent of the digital 100. Meanwhile the two counters 182 and 184 have been reset by the pulse from 116 collector and have been enabled by the 74 output changing state. The pulse train is sent into both the 10 digit counter 184 and the 3 digit BCD counter 182 and is accumulated there during the approximately 8 milliseconds of the sampling period. Those counters are then disabled. The value in the three digit BCD counter 182 is identical to the value of the 10 bit counter 184 only in the encoded format of the BCD as opposed to the binary encoding. The three digit BCD number is then fed directly onto the display 198, allowing the operator to observe the so called raw value of the control signal which should be somewhere between 50 and 999. Thus there is a wide range of response variations which are allowed for this control signal, namely of practically a 20 to 1 dynamic range for inputs.

The 10 bit counter 184 now contains a binary representation of the control EMG signal in integrated form. The operator now opens the preset switch 188. This whole process takes less than a second. Opening the switch 188 prevents the 10 bit counter 184 from being enabled or reset by subsequent signals and allows the 10 bit value stored in that counter to be fed directly through to the D to A convertor.

The output of the D to A converter then instantly assumes the voltage equivalent of whatever the digital integral of the EMG signal happen to be. As mentioned, this can be somewhere between 50 to 199. Note: The counter has a capability of storing numbers up to 1023 but the output counter can only display up to 999.

The output voltage of the D to A convertor 178 now corresponds to the integrated value of the control EMG and will be used as the reference voltage for the voltage to frequency convertor 180 for all subsequent signal collections. To collect and store a sample EMG the operator merely presses stimulus switch 32 or sets the iterate switch. The amplifier 10, the high speed integrator 174 and the comparator 176 work in identical fashion as mentioned before except that the comparator reference voltage is now proportional to the integrated control voltage. The ten bit counter 184 is not affected by the two reset and enabling control signals and maintains its count. The three digit BCD counter is reset and enabled appropriately and at the end of the 8 millisecond window contains the new EMG signal as a fraction of the control signal.

The signal then is immediately displayed on the LCD display 198 and the operator can then observe that and note whatever physiological indications this may give.

The terms and expressions which have been employed here are used as terms of description and not of limitation, and there is no intention, in the use of such terms and expressions of excluding equivalents of the features shown and described, or portions thereof, it being recognized that various modifications are possible within the scope of the invention claimed.

What is claimed is:

1. Apparatus for monitoring the neuromuscular transmission of a motor nerve and the muscle associated with the nerve in a patient, the apparatus comprising stimulator means for generating a plurality of electrical stimulus signals which are spaced apart by predetermined periods of time and for applying such stimulus signals to the motor nerve to supramaximally stimulate it, amplifier and detector means connected to the stimulator means, and including a pair of sensing electrodes adapted to be attached to the patient, for sensing the electromyogram (EMG) produced by the associated muscle as a result of the stimulating electrical signals and for amplifying the EMG, electronic integrator means connected to the amplifier and detector means for receiving each amplified EMG in response to each stimulus signal and for integrating it with respect to time over periods which fall between stimulus signals, control standard means connected to the integrator means for storing a representation of a first integrated EMG, comparator means connected to the integrator means for generating an output signal which is representative of the ratio of a select, integrated EMG and the first, integrated EMG, and means for displaying the output signal of the comparator means.

2. Apparatus as recited in claim 1 wherein the control standard means produce a reference signal representative of the integrated and stored first EMG, and wherein the comparator means include means for resetting the integrator means to a predetermined initial value whenever the integrated EMG output of the integrator means exceeds the reference signal.

3. Apparatus as recited in claims 1 or 2 wherein the comparator means generate an output signal which is representative of the ratio of the integrated, amplified EMG's obtained from a patient after the administration of a muscle relaxant drug to the first integrated EMG when taken with the monitoring apparatus before the administration of a muscle relaxant drug.

4. Apparatus as recited in claim 1 wherein the stimulator means comprise a mode control circuit for selectively producing either a single pulse, a rapid series of pulses, or a predetermined number of pulses at regular intervals.

5. Apparatus as recited in claim 1 wherein the amplifier and detector means further comprise a rectifier for passing only negative polarity EMG's.

6. Apparatus as recited in claim 1 wherein the integrating means integrates over a period of up to 8 milliseconds.

7. A method of monitoring meuromuscular blockage in a patient comprising the steps of electrically, supramaximally stimulating a motor nerve of a patient before the administration of a muscle relaxant drug, detecting amplifying the resulting electromyogram (EMG) produced by the muscle associated with the stimulated motor nerve, integrating and holding the amplified EMG with respect to time to obtain an integrated control EMG, repeating the stimulating, amplifying, integrating and holding steps after the administration of a muscle relaxant drug to the patient to obtain a second integrated EMG, and displaying the ratio of the second integrated EMG to the integrated control EMG.

8. The method as recited in claim 7 comprising the further steps of repeating the stimulating, amplifying, and integrating steps after the administration of an antagonist drug to obtain a third integrated EMG and displaying the ratio of the third integrated EMG to the integrated control EMG.

9. The method as recited in claims 7 or 8 wherein in performing the repeated integrating steps the rate of integration is adjusted to be reference to a function of the integrated control EMG.

* * * * *